United States Patent
Fukuda et al.

(10) Patent No.: US 6,733,958 B2
(45) Date of Patent: May 11, 2004

(54) MATERIAL FOR PHOTO-ALIGNMENT LAYER, PHOTO-ALIGNMENT LAYER AND METHOD OF MANUFACTURING THE SAME

(75) Inventors: Masanobu Fukuda, Sakura (JP); Hitoshi Hayakawa, Yachiyo (JP); Hirokazu Takada, Sakura (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 314 days.

(21) Appl. No.: 09/935,750

(22) Filed: Aug. 24, 2001

(65) Prior Publication Data

US 2002/0034709 A1 Mar. 21, 2002

(30) Foreign Application Priority Data

Aug. 30, 2000 (JP) ..................... P2000-260764

(51) Int. Cl.$^7$ ..................... G02F 1/1337; C07D 207/448
(52) U.S. Cl. ..................... 430/321; 428/1.26; 349/124; 522/167
(58) Field of Search .................. 430/20, 320, 321; 428/1.26; 349/124; 522/63, 167

(56) References Cited

U.S. PATENT DOCUMENTS 4,691,025 A  9/1987 Domeier et al. ............ 548/521
6,048,928 A  4/2000 Yu et al. ..................... 525/35

FOREIGN PATENT DOCUMENTS

| JP | 2001-122981 A | * | 5/2001 |
| WO | WO 00/10974 | | 3/2000 |
| WO | WO 01/38931 A1 | * | 5/2001 |

* cited by examiner

*Primary Examiner*—John A. McPherson
(74) *Attorney, Agent, or Firm*—Armstrong, Kratz, Quintos, Hanson & Brooks, LLP

(57) ABSTRACT

The present invention provides a photo-alignment layer for a liquid crystal display device, which has good liquid crystal display device characteristics such as a good voltage holding ratio and also has good alignment stability and sufficient resistance to light and heat. The photo-alignment layer is manufactured by coating a polymerizable monomer having at least one photo-alignment moiety, which carries out a photo-alignment function by the photo dimerization reaction, and at least two polymerizable maleimide groups per molecule on a substrate, and exposing the coating layer to light to cause the photo dimerization reaction of the structural unit and the photopolymerization reaction of the polymerizable maleimide group, thereby to form a crosslinked polymeric layer and to enable the polymeric layer to carry out the photo-alignment function.

9 Claims, No Drawings

MATERIAL FOR PHOTO-ALIGNMENT LAYER, PHOTO-ALIGNMENT LAYER AND METHOD OF MANUFACTURING THE SAME

BACKGROUND OF THE INVENTION

1. Field of the Invention

The present invention relates to a photo-alignment layer used in a liquid crystal display device and, more particularly, to a material for forming a photo-alignment layer, capable of aligning liquid crystal molecules by light exposure, without being subject to a rubbing treatment, a photo-alignment layer made of the material, a method of manufacturing the same, and a liquid crystal display device using the photo-alignment layer.

2. Description of Related Art

In the liquid crystal display device, the state of molecular alignment of liquid crystals is changed by the action of an electric field and a change in optical characteristics attending the change is utilized for display.

In general, liquid crystals are used while interposed in the space between the two substrates. To align liquid crystal molecules in a specific orientation, the interior surfaces of the substrates are subjected to an alignment treatment.

The alignment treatment is usually performed by a rubbing method in which a layer made of a polymer such as a polyimide is formed on a substrate made of such as glass and then rubbed with a cloth in one direction. Consequently, liquid crystal molecules near the substrate are aligned so that their directors become parallel to the rubbing direction. For example, in a twist nematic (TN) cell, two substrates coated with an alignment layer on their interior surfaces face each other between two polarizers whose polarization directions are perpendicular to each other, and the substrates are further arranged so that their rubbing directions are parallel to the polarization direction, thereby making it possible to form a display which operates based on changes in light transmittance.

Although the rubbing method has the advantage that the manufacturing apparatus has a simple structure, a cleaning process is required after the alignment treatment because dust may adhere during the manufacturing process. Also in TFT liquid crystal cells, which have recently been widely used, TFT previously deposited on the substrate may be destroyed by static electricity which is generated at the rubbing process, thus lowering the manufacturing yield. In the liquid crystal display device, since the inclination of constituent liquid crystal molecules has some directionality, problems arise, such as viewing-angle dependence in which the display color or contrast varies depending on the viewing angle.

As one method of solving the problem, for example, a multi-domain method of providing different pretilt angles (Japanese Unexamined Patent Application, First Publication No. Sho 62-159119) or alignment directions (Japanese Unexamined Patent Application, First Publication No. Sho 63-106624) of the liquid crystal molecules for different regions obtained by dividing each pixel, has been proposed. Such multi-domain is not suited for rubbing alignment method because of the complicated process required.

To solve these problems, there has recently been interest in liquid crystal alignment controlling techniques which do not use rubbing. As non-rubbing alignment techniques, for example, the oblique evaporation, LB (Langmuir Blodgett's) layer, photolithography and photo-alignment methods have been studied. Among these methods, the photo-alignment method, in which a coating layer formed on a substrate is exposed to polarized light to provide a liquid crystal aligning property, is simple and does not require a cleaning process after the alignment treatment, and multi-domain can also easily be performed by using such as photo-mask method. Therefore, the photo-alignment method has been intensively studied. As the photo-alignment method, a method utilizing photoisomerization of a photo-alignment moiety (e.g. an azo group) capable of carrying out a photo-alignment function in organic molecules, a method utilizing photo dimerization of a cinnamoyl group, a coumarin group or a chalcone group, a method utilizing photocrosslinking of a benzophenone group, and a method utilizing photodegradation of a polyimide resin have been reported.

As the material for the photo-alignment layer, which utilizes photoisomerization, photo dimerization or photocrosslinking, a polymeric material is often used to obtain a uniform layer when coated on a substrate made of such as glass, and the photo-alignment moiety is often introduced into the side chain or the main chain of the polymeric material. It is also possible to use a material prepared by using molecules having a photo-alignment property as guest molecules and dispersing them in a host compound consisting of a polymeric compound.

However, the photoisomerized materials is inferior in photostability after the photo-alignment treatment because it utilizes cis-trans photoisomerization of molecules by exposure to polarized UV. In the case of photo-degradated materials, since the liquid crystal is contaminated with the degradation product produced during the photo-alignment treatment, the substrate must be cleaned after the treatment, thereby losing the feature that no cleaning of the photo-alignment layer is required. Further, almost all photo-alignment materials using the polymeric material have the problem that the kind of a solvent used when coated on the substrate is limited because of their poor solubility in solvents.

For example, WO9637807 (U.S. Pat. No. 6,001,277, Japanese Unexamined Patent Application, First Publication No. Hei 8-328005) discloses a liquid crystal layer using a resin having a photoisomerizable structural unit, which exhibits dichroizm, and a reactive functional group. This material is a polymeric compound and the kind of the solvent used when coated on the substrate is limited, and a high-boiling point polar solvent such as N,N-dimethylacetamide or N-methyl-2-pyrolidone is used. In this case, a long time is required to evaporate the solvent after coating, thereby lowering the productivity. Furthermore, this material has a low crosslink density because of the small proportion of reactive functional groups in the resin. As a result, the heat resistance of the alignment layer made of this material is not always sufficient.

Examples of the method to solve these problems, thereby achieving a durable and stable liquid crystal aligning property of the photo-alignment layer include a method of thermally polymerizing or photopolymerizing a polymerizable monomer having a photo-alignment moiety, which shows an alignment property upon exposure to polarized light, and photo-aligning the resulting polymer by exposure to polarized light. In general, however, it becomes necessary to add a polymerization initiator to thermally polymerize or photopolymerize the monomer. Since this polymerization initiator is a low-molecular weight compound, the polymerization initiator diffuses into the liquid crystal in the cell with the lapse of long periods of time and thus the characteristics of the liquid crystal display device (e.g. voltage holding ratio) are likely to be deteriorated.

A photopolymerizable group which does not require a polymerization initiator is a polymerizable maleimide group. A photo-alignment layer using a compound having this polymerizable maleimide group is disclosed in Japanese Unexamined Patent Application, First Publication No. 2000-53766 (U.S. Pat. No. 6,218,501) and Japanese Patent No. 2962473 (Japanese Unexamined Patent Application, First Publication No. Hei 11-2815, U.S. Pat. No. 6,048,928). Although in these photo-alignment layers, a functional group capable of inducing photo-alignment is added as a side chain to the main chain of polymaleimide, these photo-alignment layers are still insufficient in the long-term stability of their heat resistance and liquid crystal alignment capability.

BRIEF SUMMARY OF THE INVENTION

An object to be achieved by the present invention is to provide a photo-alignment layer for liquid crystal display devices, which has good liquid crystal display device characteristics such as a high voltage holding ratio and also has good alignment stability and sufficient resistance to light and heat.

To achieve the object described above, the present invention provides a material for a photo-alignment layer, comprising a polymerizable monomer having at least one photo-alignment moiety, which carries out a photo-alignment function by the photo dimerization reaction, and at least two polymerizable maleimide groups per molecule.

To achieve the object described above, the present invention also provides a photo-alignment layer comprising a polymer of a polymerizable monomer having at least one photo-alignment moiety, which carries out a photo-alignment function by the photo dimerization reaction, and at least two polymerizable maleimide groups per molecule, the photo-alignment layer having the photo-alignment function carried out by photo dimerization of the photo-alignment moiety and a crosslinked structure formed by polymerization of the polymerizable maleimide group.

To achieve the object described above, the present invention further provides a method of manufacturing a photo-alignment layer, which comprises coating a polymerizable monomer having at least one photo-alignment moiety, which carries out a photo-alignment function by the photo dimerization reaction, and at least two polymerizable maleimide groups per molecule on a substrate, and irradiating the coating layer with light to cause the photo dimerization reaction of the photo-alignment moiety causing photo-alignment by a photo dimerization and the photopolymization reaction of the polymerizable maleimide group, thereby to form a crosslinked polymeric layer and to enable the polymeric layer to carry out the photo-alignment function.

To achieve the object described above, the present invention further provides a method of manufacturing a photo-alignment layer, which comprises coating a polymerizable monomer having at least one photo-alignment moiety, which carries out a photo-alignment function by the photo dimerization reaction, and at least two polymerizable maleimide groups per molecule on a substrate, heating the coating layer to cause the thermal polymerizable reaction, thereby to form a crosslinked polymeric layer, and exposing the polymeric layer to light to cause the photo dimerization reaction of the photo-alignment moiety causing photo-alignment by a photo dimerization, thereby to enable the polymeric layer to carry out the photo-alignment function.

To achieve the object described above, the present invention further provides a liquid crystal display device having a structure comprising two substrates each having an alignment layer on its interior surface and liquid crystals interposed between two substrates, wherein the alignment layer is a photo-alignment layer which comprises a polymer of a polymerizable monomer having at least one photo-alignment moiety, which carries out a photo-alignment function by the photo dimerization reaction, and at least two polymerizable maleimide groups per molecule, and also has the photo-alignment function carried out by photo dimerization of the photo-alignment moiety and a crosslinked structure formed by polymerization of the polymerizable maleimide group.

By using the material for the photo-alignment layer made of a maleimide derivative of the present invention, it is possible to obtain a photo-alignment layer which has good liquid crystal display device characteristics such as high voltage holding ratio and also has a good alignment stability and sufficient resistance to light and heat.

DETAILED DESCRIPTION OF THE INVENTION

In the polymerizable monomer having at least one photo-alignment moiety, which carries out a photo-alignment function by the photo dimerization reaction, and at least two polymerizable maleimide groups per molecule, which is used in the material for the photo-alignment layer of the present invention, the photo-alignment moiety is not specifically limited as far as it is a functional group which causes a photo reaction capable of providing an alignment property due to dimerization by exposure to polarized light. Particularly, a structural unit having at least one double bond (excluding double bonds which constitute aromatic rings) represented by C=C or C=O is preferably used.

The basic structure of the photo-alignment moiety, which carries out a photo-alignment function due to the photo dimerization reaction, includes the following.

Examples of the photo-alignment moiety having a C=C bond, which carries out a photo-alignment function due to the photo dimerization reaction, include groups having a structure such as a polyene group, stilbene group, stilbazole group, stilbazolium group, cinnamoyl group, hemithioindigo group, or chalcone group. Examples of the photo-alignment moiety having a C=O bond, which carries out a photo-alignment function by the photo dimerization reaction, include groups having a structure such as a benzophenone group or coumarin group.

Specific examples thereof include groups having the following structure. As a matter of course, these structures may have a substituent such as an alkyl group, alkoxy group, aryl group, allyloxy group, cyano group, alkoxycarbonyl group, hydroxyl group, sulfonic acid group, or alkyl halide group.

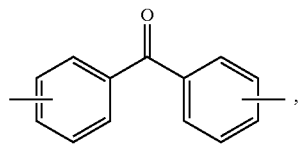

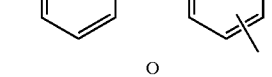

Specifically, the polymerizable monomer having at least one photo-alignment moiety, which carries out a photo-alignment function by the photo dimerization reaction, and at least two polymerizable maleimide groups per molecule, is preferably a compound represented by the general formula (1):

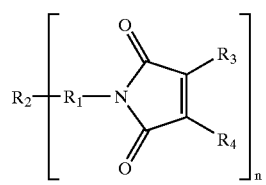

and a compound represented by the general formula (2):

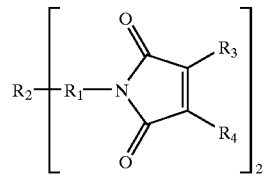

is particularly preferred.

In the general formulas (1) and (2), $R_1$ represents at least one group selected from the group consisting of straight-chain or branched alkylene groups having 1 to 30 carbon atoms, cycloalkylene groups having 3 to 12 carbon atoms, arylalkylene group and cycloalkylalkylene groups.

Specific examples of the organic group as for $R_1$ include straight-chain alkylene groups such as a methylene group, ethylene group, trimethylene group, tetramethylene group, pentamethylene group, hexamethylene group, heptamethylene group, octamethylene group, nonamethylene group, decamethylene group, undecamethylene group, or dodecamethylene group; alkylene groups having a branched alkyl group, such as a 1-methylethylene group, 1-methyl-trimethylene group, 2-methyl-trimethylene group, 1-methyl-tetramethylene group, 2-methyl-tetramethylene group, 1-methyl-pentamethylene group, 2-methyl-pentamethylene group, 3-methyl-pentamethylene group, or 2,2-dimethyl-trimethylene group; cycloalkylene groups such as a cyclopentylene group or cyclohexylene group; arylalkylene groups having an aryl group in the main chain or side chain, such as a benzylene group, 2,2-diphenyl-trimethylene group, 1-phenyl-ethylene group, or 1-phenyl-tetraethylene group; and cycloalkyl-alkylene groups having a cycloallkyl group in the main chain or side chain, such as a cyclohexylmethylene group, 1-cyclohexyl-ethylene group, or 1-cyclohexyl-tetraethylene group. Among these organic groups, an alkylene group having 1 to 30 carbon atoms or a cycloalkylene group having 3 to 12 carbon atoms is preferred.

$R_1$ may also be a group in which these 2 to 5 groups are combined via a single bond, an ester bond, an ether bond or urethane bond.

Examples of the combined group include group composed of (poly)ether in which at least two alkylene groups are combined via an ether bond, group composed of (poly)ester in which at least two alkylene groups are combined via an ester bond, group composed of (poly)urethane in which at least two alkylene groups are combined via a urethane bond, and groups composed of {(poly)ether(poly)ol} (poly)carboxylate obtained by esterifying (poly)ether(poly)ol in which at least two alkylene groups are combined via an ether bond with (poly)carboxylic acid.

In the general formulas (1) and (2), $R_2$ represents the above-described photo-alignment moiety, which carries out a photo-alignment function by the above-described photo dimerization reaction.

Among the photo-alignment moieties which carry out a photo-alignment function by the photo dimerization reaction, a photo-alignment material having a benzophenone structure using a maleimide derivative having a photo-alignment moiety, which carries out a photo-alignment function, is particularly preferred because it requires a small exposure energy of polarized light to carry out a photo-alignment function and is also superior in heat stability and storage stability of the resulting photo-alignment layer.

In the compounds represented by the general formulas (1) and (2), the photo-alignment moiety represented by $R_2$, which carries out a photo-alignment function by the photo dimerization reaction, and the group represented by $R_1$ are combined via a single bond, an ester bond or a urethane bond. Although the number of bonding of photo-alignment moieties which carry out a photo-alignment function by the photo dimerization reaction is the same as that of a polymerizable maleimide group per molecule, the maleimide derivative used in the present invention has a plurality of polymerizable maleimide groups and, therefore, the number is preferably within a range from 2 to 4. Particularly, the number of the bonding of the photo-alignment moieties which carry out a photo-alignment function by the photo dimerization reaction is preferably 2 because the polymerization of the polymerizable maleimide group easily proceeds to form a stable maleimide polymer and the exposure energy required to induce photo dimerization of the photo-alignment moiety which carries out a photo-alignment function is comparatively small.

In the general formulas (1) and (2), $R_3$ and $R_4$ each independently represents a hydrogen atom, an alkyl group having 1 to 8 carbon atoms, a phenyl group, or a halogen atom.

In the general formula (1), n represents an integer of 2 to 4. Among these compounds, a compound represented by the general formula (2) in which n is 2 is particularly preferred because the polymerization of the polymerizable maleimide group easily proceeds to form a stable maleimide polymer and the exposure energy required to induce photo alignment of the photo-alignment moiety which carries out a photo-alignment function is comparatively small.

The photo-alignment material of the present invention may appropriately contain a maleimide compound represented by the following general formula (3) for the purpose of improving the alignment of liquid crystal molecules by adjusting the density of the added photo-alignment moieties represented by $R_2$, which carry out a photo-alignment function by the photo dimerization reaction, or improving the coatability on the substrate by enhancing the solubility in the solvent. To obtain good sensitivity to light exposure for photo-alignment, the maleimide derivative represented by the general formula (2), which has a photo-alignment moiety capable of carrying out a photo-alignment function by the photo dimerization reaction, may be copolymerized with a maleimide derivative represented by the general formula (3):

which does not have a photo-alignment moiety capable of carrying out a photo-alignment function by the photo dimerization reaction. The ratio of the maleimide derivative to be mixed in, which does not have a photo-alignment moiety capable of carrying out a photo-alignment function by the photo dimerization reaction, is preferably within a range from 0 to 80% by weight, and particularly preferably from 0 to 50% by weight, based on the total weight.

In the general formula (3), $R_7$ represents at least one group selected from the group consisting of (i) straight-chain alkylene groups having 1 to 30 carbon atoms, (ii) branched alkylene groups having 1 to 30 carbon atoms, (iii) cycloalkylene groups having 3 to 12 carbon atoms, (iv) arylalkylene groups and (v) cycloalkylalkylene groups. $R_5$ and $R_6$ each independently represents a hydrogen atom, an alkyl group having 1 to 8 carbon atoms, a phenyl group, or a halogen atom.

Specific examples of $R_7$ in the general formula (3) include straight-chain alkylene groups such as a methylene group, ethylene group, trimethylene group, tetramethylene group, pentamethylene group, hexamethylene group, heptamethylene group, octamethylene group, nonamethylene group, decamethylene group, undecamethylene group, or dodecamethylene group; alkylene groups having a branched alkyl group, such as a 1-methylethylene group, 1-methyl-trimethylene group, 2-methyl-trimethylene group, 1-methyl-tetramethylene group, 2-methyl-tetramethylene group, 1-methyl-pentamethylene group, 2-methyl-pentamethylene group, 3-methyl-pentamethylene group, or 2,2-dimethyl-trimethylene group; cycloalkylene groups such as a cyclopentylene group or cyclohexylene group; arylalkylene groups having an aryl group in the main chain or side chain, such as a benzylene group, 2,2-diphenyl-trimethylene group, 1-phenyl-ethylene group, or 1-phenyl-tetraethylene group; and cycloalkyl-alkylene groups having a cycloallkyl group in the main chain or side chain, such as a cyclohexylmethylene group, 1-cyclohexyl-ethylene group, or 1-cyclohexyl-tetraethylene group.

$R_7$ in the general formula (3) may also be a group in which a plurality of the groups described above are combined via a single bond, an ester bond, an ether bond or a urethane bond.

Examples of the combined group include groups composed of (poly)ether in which at least two alkylene groups are combined via an ether bond, groups composed of (poly)ester in which at least two alkylene groups are combined via an ester bond, groups composed of (poly)urethane in which at least two alkylene groups are combined via a (poly)urethane bond, and groups composed of {(poly)ether(poly)ol} (poly)carboxylate obtained by esterifying (poly)ether (poly)ol in which at least two alkylene groups are combined via an ether bond with (poly)carboxylic acid.

Embodiments of the method of manufacturing a photo-alignment layer and a liquid crystal display device including the same using the material for the photo-alignment layer of the present invention will now be described.

First, the photo-alignment material of the present invention is used after dissolving in an appropriate solvent. N-methylpyrrolidone, dimethylformamide, butylcellosolve, γ-butyrolactone, chlorobenzene, dimethyl sulfoxide, dimethylacetamide and tetrahydrofuran are generally used, though the solvent is not specifically limited thereto. Among these solvents, butylcellosolve and γ-butyrolactone are particularly preferred because the coatability is good and a uniform layer can be obtained. These solvents can also be used in combination taking the coatability and volatilization of the solvent shortly after coating into consideration.

The solution of the photo-alignment material is coated onto the substrate by a method such as spin coating or a printing method and, after drying, the polymerization and photo-alignment operation of the polymerizable maleimide group are conducted.

The substrate used in the present invention is a substrate which is conventionally used in the photo-alignment layer and has enough heat resistance to withstand thermocuring. A glass substrate can be such a substrate.

The polymerization operation of the polymerizable maleimide group due to light or heat is preferably conducted before the alignment operation because the photo dimerization reaction is likely to exert an adverse effect on the photo-aligned structural unit.

The polymerizable maleimide group is polymerized by exposure to light such as UV light, or by heating. When light exposure is carried out, light having a wavelength which does not induce a photo-alignment function of the photo-alignment moiety is preferably used. However, polymerization by heating is more preferably conducted before the photo-alignment operation because the solvent used when the substrate is coated can also be dried. To completely polymerize the polymerizable maleimide group, the polymerization is conducted by light exposure or heating and the operation of inducing photo-alignment by light exposure and, moreover, heating or exposure to non-polarized light suited for photopolymerization of the polymerizable maleimide group may be carried out in sequence.

If the wavelength of the light used to polymerize the polymerizable maleimide group is close to the wavelength of the light used to carry out the photo-alignment function, the polymerization of the polymerizable maleimide group and the operation of carrying out the photo-alignment function can be simultaneously conducted by only one light exposure. Although the exposed light used in the photopolymerization of the polymerizable maleimide group is not specifically limited, UV is preferably used. Also the exposure method is not specifically limited and it is possible to use light having a polarization state such as non-polarized light, linearly polarized light, elliptically polarized light or the like.

The operation of inducing photo-alignment by the photo dimerization reaction is conducted by exposing to polarized light. A wavelength capable of efficiently dimerizing the photo-aligning group is selected as the wavelength of the polarized light and examples of light having such a wavelength include visible and UV light. Particularly, UV is preferred. Linearly polarized light and elliptically polarized light are often used as the polarized light. To obtain a pretilt of the liquid crystal, a method of exposure to polarized light in a direction oblique to the substrate, and a method of exposure to non-polarized light in an oblique direction after exposure to polarized light may be used.

According to the present invention, a photo-alignment layer is obtained by coating a material for the photo-alignment layer containing a polymerizable monomer having a photo-alignment moiety, which carries out a photo-alignment function by a photo dimerization reaction, and plural polymerizable maleimide groups per molecule on a substrate, polymerizing the polymerizable maleimide groups and inducing the photo dimerization reaction of the photo-alignment moiety which carries out the photo-alignment function. The maleimide compound used in the present invention has the feature that it has high solubility in a solvent because of its low molecular weight, and is easily coated. According to the present invention, a photo-alignment layer having high stability against light and heat can be obtained because a crosslinked structure is formed by copolymerization of a polymerizable maleimide group and also photo-alignment is realized by the photo dimerization reaction of the photo-alignment moiety.

Since the polymerization due to the maleimide group does not require a polymerization initiator, it is made possible to eliminate the cause for the deterioration in the performance of liquid crystal display devices (e.g. the reduction of the voltage holding ratio) without causing the polymerization initiator to dissolve in the liquid crystal after forming the liquid crystal cell.

EXAMPLES

The following Synthesis Examples, Examples and Comparative Examples further illustrate the present invention in detail, but the present invention is not limited by these Examples.

Synthesis Example 1

Synthesis of Material for Maleimide Photo-alignment Layer Having Benzophenone Structure (a) Synthesis of Maleimideacetic Acid In a 500 ml four-necked flask equipped with a stirrer, a thermometer, a dropping funnel, a Dean-Stark fractional distillator and a condenser tube, 140 g of toluene, 5.2 g of p-toluenesulfonic acid monohydrate and 2.8 g of triethylamine were added in sequence and, after adding 30 g of maleic anhydride while stirring, the mixture was dissolved while heating to 30° C. After 23 g of glycine was further added, the reaction was conducted while stirring at 70° C. for three hours. After adding 50 g of toluene and 60 g of triethylamine, the solvent was heated at reflux and the reaction was conducted for one hour while removing water. To the residue obtained by distilling off the solvent from the reaction mixture, 4 mol/dm$^3$ of hydrochloric acid was added to adjust the pH to 2, followed by heating and recrystallization to obtain 7.3 g of maleimideacetic acid as a pale yellow solid.

(b) Synthesis of 4,4'-bis(2-hydroxyethoxy)benzophenone

In a 300 ml four-necked flask equipped with a stirrer, a thermometer, a dropping funnel and a condenser tube, 62.5 g of 2-bromoethanol was added and 100 g of N-methylpyrrolidone was added while stirring under cooling with an ice bath. To the mixture, 10 mg of p-toluenesulfonic acid monohydrate was added and 42.1 g of dihydropyran was added dropwise over about 10 minutes. After stirring under cooling with ice for two hours and further stirring at room temperature for two hours, 42.8 g of 4,4'-dihydroxybenzophenone and 69.1 g of potassium carbonate were added and the reaction was conducted at 120° C. for three hours. After cooling, the reaction mixture was added to 400 ml of water and the solution was extracted twice with 400 ml of toluene. The resulting toluene layer was dried over anhydrous sodium sulfate and the solvent was distilled off by an evaporator.

To the resulting residue, 450 g of methanol, 70 g of water and 1.0 g of concentrated hydrochloric acid were added, followed by stirring overnight. The resulting precipitate was collected by filtration, washed sufficiently with methanol, and then dried to obtain 52 g of 4,4'-bis(2-hydroxyethoxy) benzophenone.

(c) Synthesis of Material for Maleimide Photo-alignment Layer

In a 500 ml four-necked flask equipped with a stirrer, a thermometer, a Dean-Stark fractional distillator and a condenser tube, 8.8 g of the maleimideacetic acid obtained in Synthesis Example 1 (a), 6.1 g of 4,4'-bis(2-hydroxyethoxy) benzophenone, 0.4 g of p-toluenesulfonic acid monohydrate, 20 mg of hydroquinone and 150 ml of toluene were added in sequence. The solvent was refluxed by heating to 90° C. under reduced pressure and the reaction was conducted for 15 hours while removing water. After the completion of the reaction, the reaction mixture was filtered while being kept in a hot condition and the resulting solid was sufficiently washed with methanol and dried to obtain 8.6 g of a material for a difunctional maleimide photo-alignment layer represented by the formula (4):

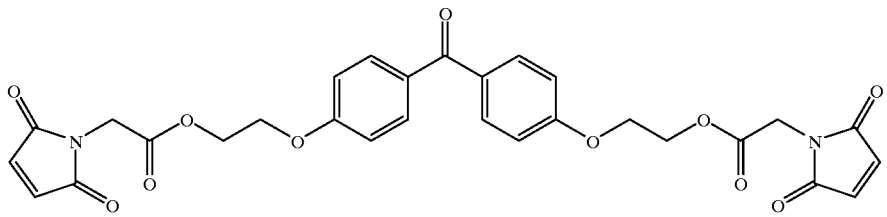

Synthesis Example 2

Synthesis of Maleimide Derivative Having no Benzophenone Structure

In a 500 ml four-necked flask equipped with a stirrer, a thermometer, a Dean-Stark fractional distillator and a condenser tube, 8.8 g of the maleimideacetic acid obtained in Synthesis Example 1 (a), 5.0 g of polypropylene glycol having a number-average molecular weight of 400, 0.4 g of p-toluenesulfonic acid monohydrate, 20 mg of hydroquinone and 150 ml of toluene were added in sequence. The solvent was refluxed by heating to 90° C. under reduced pressure and the reaction was conducted for 15 hours while removing water. After the completion of the reaction, the reaction mixture was washed twice with a diluted sodium hydroxide solution and then washed three times with pure water, and then toluene was distilled off to obtain 7.7 g of a difunctional maleimide derivative represented by the formula (5):

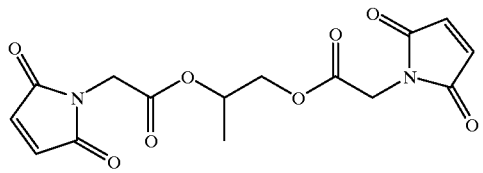

Synthesis Example 3

Synthesis of Maleimide Derivative Having Cinnamoyl Group (a) Synthesis of 4-(2-hydroxyethoxy)cinnamic Acid-2-hydroxyethyl ester In a 500 ml autoclave, a mixed solution of 40.0 g (1.0 mol) of sodium hydroxide in 80 ml of ethanol and 100 ml of water was added and, after adding 82.1 g (0.5 mol) of 4-hydroxycinnamic acid, the mixture was dissolved. While cooling with ice, 132.2 g (3.0 mol) of oxysilane was added and, after sealing the autoclave, the reaction was conducted at 80° C. for six hours. The reaction solution was diluted by adding 200 ml of water and the diluted solution was extracted twice with 100 ml of ethyl acetate. After the extract was purified by silica gel chromatography, ethyl acetate was distilled off under reduced pressure and the residue was concentrated to dryness and then recrystallized from butanol to obtain 90.8 g (72%) of 4-(2-hydroxyethoxy)cinnamic acid-2-hydroxyethyl ester.

(b) Synthesis of Maleimide Derivative Having Cinnamoyl Group

In a 500 ml four-necked flask equipped with a stirrer, a thermometer, a Dean-Stark fractional distillator and a condenser tube, 8.8 g of the maleimideacetic acid obtained in Synthesis Example 1 (a), 5.1 g of the 4-(2-hydroxyethoxy) cinnamic acid-2-hydroxyethyl ester obtained in Synthesis Example 3 (a), 0.4 g of p-toluenesulfonic acid monohydrate, 20 mg of hydroquinone and 150 ml of toluene were added in sequence. The solvent was refluxed by heating to 90° C. under reduced pressure and the reaction was conducted for 15 hours while removing water. After the completion of the reaction, the reaction mixture was filtered while being kept in a hot condition and the resulting solid was sufficiently washed with methanol and dried to obtain 7.8 g of a material for a difunctional maleimide derivative represented by the formula (6):

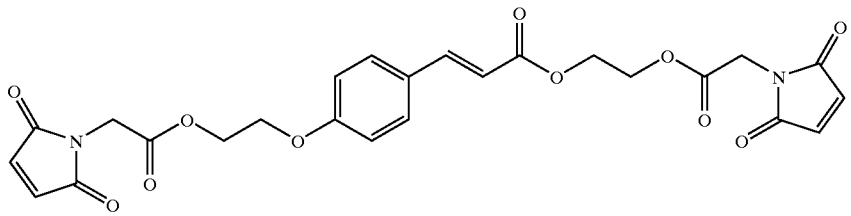

$^1$H-NMR (300 MHz, $(CD_3)_2SO$) δ=3.75–4.47 (m, 12H), 6.84–7.15 (m, 8H), 7.63–8.18 (m, 6H)

Comparative Synthesis Example 1

In the same manner as in Synthesis Example 1 (c); synthesis of the maleimide derivative was carried out, except that acrylic acid was used in place of maleimideacetic acid, and a difunctional acrylate represented by the formula (7):

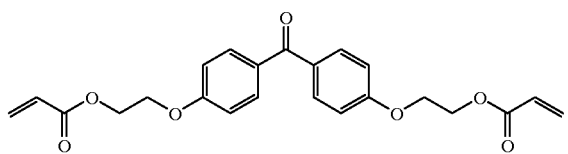

was obtained.

Comparative Synthesis Example 2

Synthesis of Material for Photo-alignment Layer Having Polyimide in the Main Chain and Parafluorobenzoylcinnamoyl Group in the Side Chain (a) Synthesis of Polyhydroxyphenylmaleimide In a three-necked round flask filled with nitrogen, 5 g of a maleic anhydride polymer (manufactured by Polyscience Co., U.S.A) and 3 g of aminophenol were mixed with 100 ml of xylene, followed by stirring at normal temperature for 30 minutes. Furthermore, 2.9 g of isoquinoline was added and, after gradually raising the temperature to 150° C., the reaction was continued for about three hours while removing water produced during the reaction. After confirming that production of water was stopped, the reaction was completed and the temperature was reduced to normal temperature. The reaction solution was poured into 500 ml of methanol to precipitate the product, which was collected by filtration under reduced pressure and then dried at 100° C. under reduced pressure to obtain polyhydroxyphenylmaleimide.

(b) Synthesis of Parafluorobenzoylcinnamoyl Chloride 16.42 g (0.1 mol) of parahydroxycinnamic acid and 8 g of sodium hydroxide were dissolved in 100 ml of water and 100 ml of dimethyl sulfoxide (DMSO) and 15.86 g (0.1 mol) of parafluorobenzoyl chloride was gradually added dropwise while vigorously stirring at 0° C. After the reaction was conducted at normal temperature for about two hours, the reaction solution was neutralized with diluted hydrochloric acid, thereby to adjust the pH within a range from 6 to 7. The resulting solid-like intermediate was collected by filtration and then completely washed with water. After completely drying under a vacuum, the resulting product was recrystallized from ethanol to obtain parafluorobenzoyloxycinnamic acid with a yield of 90%. To the resulting parafluorobenzoyloxycinnamic acid, 1.2 eq. of thionyl chloride and about 50 ml of methylene chloride were added and the reaction was conducted until a solution, which is transparent at normal temperature, is obtained. After the completion of the reaction, the solvent and thionyl chloride were removed under reduced pressure and the reaction product was completely dried to obtain parafluorobenzoylcinnamoyl chloride.

(c) Synthesis of Material for Photo-alignment Layer Having Polymaleimide in the Main Chain and Parafluorobenzoylcinnamoyl Group in the Side Chain After 1.7 g of the polyhydroxyphenyl maleimide obtained in Comparative Synthesis Example 2 (a) was dissolved in 50 ml of N-methylpyrrolidone (NMP), 1.0 g of triethylamine was added, followed by stirring for 30 minutes. The reaction temperature was reduced to 5° C., and 2.13 g of the parafluorobenzoylcinnamoyl chloride obtained in Comparative Synthesis Example 2 (b) was slowly added dropwise while vigorously stirring. After the dropwise addition of parafluorobenzoylcinnamoyl chloride was completed, stirring was continued for about one hour and the reaction was completed. The reaction solution was poured into a beaker in which 200 ml of water and 200 ml of methanol are mixed, thereby to precipitate the product, which was sufficiently washed with excess water and methanol, filtered under reduced pressure and then dried under a vacuum to obtain a material for a photo-alignment layer having polymaleimide in the main chain and a parafluorobenzoylcinnamoyl group in the side chain.

Using the materials for photo-alignment layer obtained by the Synthesis Examples and Comparative Synthesis Examples described above, photo-alignment layers were made and their physical properties were evaluated. The method of making the photo-alignment layers and the method of evaluating their physical properties are as follows.

Method of Making Photo-alignment Layer (a) Preparation of Photo-alignment Material Solution The maleimide derivative obtained in the Synthesis Example was dissolved in a mixed solution of N-methylpyrrolidone and butylcellosolve in a mixing ratio of 1:1 to give a solution having a nonvolatile content of 5%, which was filtered with a filter having a pore size of 0.1 $\mu$m to obtain a solution of a material for a photo-alignment layer.

(b-1) Formation of Photo-alignment Layer (Thermocuring Method)

The solution of the material for the photo-alignment layer obtained by the method (a) was uniformly coated on a glass substrate with an ITO electrode by a spin coater, dried and then cured at 190° C. for one hour. Then, the surface of the resulting coating layer was exposed to linearly polarized UV at about 365 nm from an ultra-high pressure mercury lamp in a total energy of 30 J/cm$^2$ to form a photo-alignment layer.

(b-2) Formation of Photo-alignment Layer (Photocuring Method)

The solution of the material for the photo-alignment layer obtained by the method of (a) was uniformly coated on a glass substrate with an ITO electrode by a spin coater and dried at 100° C. for 15 minutes, and then the surface of the coating layer was exposed to UV at about 313 nm from an ultra-high pressure mercury lamp in a total energy of 2 J/cm$^2$. Then, the surface of the resulting coating layer was exposed to linearly polarized UV at about 365 nm from an ultra-high pressure mercury lamp in a total energy of 30 J/cm$^2$ to form a photo-alignment layer.

(c) Formation of Liquid Crystal Cell

An epoxy adhesive containing styrene beads having a diameter of 8 $\mu$m was coated around the periphery of one of the substrate coated by the photo-alignment layer obtained in (b-1) or (b-2), with the exception of a liquid crystal injection hole. Another substrate coated by the photo-alignment layer were laid on the substrate so that alignment surfaces faced each other, and that the plane of polarization of exposed photo-alignment layer on the one of the substrates was at a right angle to that of the other substrate, and then the adhesive was cured at 150° C. over 90 minutes.

The liquid crystal cell was filled with a nematic liquid crystal (5CB) in an isotropic phase by injecting it under a vacuum through the liquid crystal injection hole, and then the liquid crystal injection hole was sealed with an epoxy adhesive.

Method of Evaluating Photo-alignment Layer (a) Evaluation of Liquid Crystal Alignment Property The alignment property of the liquid crystal was evaluated by interposing the liquid crystal cell obtained in the method (c) into the space between the two polarizers, the plane of polarization of which are at a right angle to each other, applying a voltage of 5 V to the space between the electrodes, and switching on/off thereby to switch lighting.

(b) Measurement of Voltage Holding Ratio

To the liquid crystal cell obtained by the method (c), a DC voltage of 5 V was applied for 64 microseconds, and then a holding ratio of the voltage after opening for 16.6 milliseconds to the initially applied voltage was measured.

(c) Measurement of Durability

The alignment property was visually observed after this liquid crystal cell was allowed to stand at 80° C. for 1000 hours.

(d) Evaluation of Heat Resistance

After the photo-alignment layer obtained by the method (b-1) or (b-2) was heated at 180° C. for 60 minutes, a liquid crystal cell was made by the method (c) and the liquid crystal alignment property was visually observed.

Example 1

A solution of a material for the photo-alignment layer was prepared from the maleimide derivative (8) obtained in Synthesis Example 1 in accordance with the method of preparing the above solution of the material for the photo-alignment layer, and then a photo-alignment layer was made in accordance with the method of thermocuring the photo-alignment layer (b-1). A liquid crystal cell was made by using the resulting photo-alignment layer and its physical properties were evaluated in accordance with the above evaluation method.

As a result, the liquid crystal showed a voltage holding ratio of 99% and was superior in liquid crystal alignment property, durability and heat resistance.

Example 2

A solution of a material for the photo-alignment layer was prepared from the maleimide derivative (8) obtained in Synthesis Example 1 in accordance with the method of preparing the above solution of the material for the photo-alignment layer, and then a photo-alignment layer was made in accordance with the method of photocuring the photo-alignment layer (b-2). A liquid crystal cell was made by using the resulting photo-alignment layer and its physical properties were evaluated in accordance with the above evaluation method.

As a result, the liquid crystal showed a voltage holding ratio of 99% and was superior in liquid crystal alignment property, durability and heat resistance.

Example 3

Evaluation was conducted in the same manner as in Example 1, except that the maleimide derivative (8) obtained in Synthesis Example 1 was replaced by a mixture of the maleimide derivative (8) obtained in Synthesis Example 1 and the maleimide derivative (9) obtained in Synthesis Example 2 in a ratio of 1:1.

As a result, the liquid crystal showed a voltage holding ratio of 99% and was superior in liquid crystal alignment property, durability and heat resistance.

Example 4

Evaluation was conducted in the same manner as in Example 1, except that the maleimide derivative (8) obtained in Synthesis Example 1 was replaced by the maleimide derivative (10) obtained in Synthesis Example 3.

As a result, the liquid crystal showed a voltage holding ratio of 99% and was superior in liquid crystal alignment property, durability and heat resistance.

Comparative Example 1

Evaluation was conducted in the same manner as in Example 1, except that the maleimide derivative (8) obtained in Synthesis Example 1 was replaced by the acrylic acid derivative (11) synthesized in Comparative Synthesis Example 1 and a mixture obtained by adding 0.1% 2,2'-azobisisobutyronitrile to the acrylic acid derivative.

As a result, the liquid crystal was superior in liquid crystal alignment property, durability and heat resistance, but showed a low voltage holding ratio, such as 89%.

Comparative Example 2

Evaluation was conducted in the same manner as in Example 1, except that the maleimide derivative (8) obtained in Synthesis Example 1 was replaced by the material for the photo-alignment layer synthesized in Comparative Synthesis Example 2, which has polymaleimide in the main chain and a parafluorobenzoylcinnamoyl group in the side chain.

As a result, the liquid crystal showed a good voltage holding ratio such as 98% and was superior in liquid crystal alignment property, but switching between the on-state and the off-state, which indicate poor alignment property after the durability or heat resistance test.

What is claimed is:

1. A material for a photo-alignment layer the material comprising a polymerizable monomer, the polymerizable monomer having at least one photo-alignment moiety which causes photo-alignment by a photo dimerization reaction, and having at least two polymerizable maleimide groups in a polymerizable monomer, the polymerizable monomer represented by the general formula:

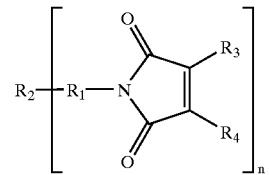

wherein:

$R_1$ represents:

an alkylene group having 1 to 30 carbon atoms, a cycloalkylene group having 3 to 12 carbon atoms, or 2 to 5 molecular groups selected from the group of alkylene groups having 1 to 30 carbon atoms and cycloalkylene groups having 3 to 12 carbon atoms, the 2 to 5 molecular groups joined via a single bond, an ester bond, an ether bond or a urethane bond;

$R_2$ represents a photo-alignment moiety selected from the group consisting of a benzophenone group, cinnamoyl group, chalcone groups and coumarin group;

$R_3$ and $R_4$ each independently represents a hydrogen atom, an alkyl group having 1 to 8 carbon atoms, a phenyl group, or a halogen atom; and n represents an integer of 2 to 4.

2. A photo-alignment layer comprising a polymer of a polymerizable monomer having at least one photo-alignment moiety, which causes a photo-alignment by a photo dimerization reaction, and having at least two polymerizable maleimide groups in a polymerizable monomer, the photo-alignment layer having the photo-alignment caused by photo dimerization of the photo-alignment moiety and a crosslinked structure formed by polymerization of the polymerizable maleimide group.

3. The photo-alignment layer according to claim 2, wherein the photo-alignment layer is produced by a polymerizable monomer having a at least two polymerizable maleimide groups is compound represented by the general formula:

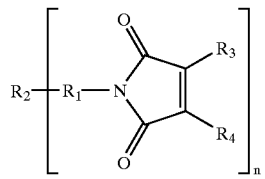

wherein:

$R_1$ represents:
an alkylene group having 1 to 30 carbon atoms, a cycloalkylene group having 3 to 12 carbon atoms, or 2 to 5 molecular groups selected from the group of alkylene groups having 1 to 30 carbon atoms and cycloalkylene groups having 3 to 12 carbon atoms, the 2 to 5 molecular groups joined via a single bond, ester bond, ether bond or urethane bond; $R_2$ represents a photo-alignment moiety selected from the group consisting of benzophenone group, cinnamoyl group, chalcone group and coumarin group;

$R_3$ and $R_4$ each independently represents a hydrogen atom, an alkyl group having 1 to 8 carbon atoms, a phenyl group, or a halogen atom; and n represents an integer of 2 to 4.

4. A method of manufacturing a photo-alignment layer, which comprises:

coating a polymerizable monomer having at least one photo-alignment moiety, which causes photo-alignment a photo dimerization reaction, and at least two polymerizable maleimide groups in a polymerizable monomer on a substrate, and irradiating the coating layer with light to cause a photo dimerization reaction of the photo-alignment moiety causing a photo-alignment by photo dimerization and the photo-polymerization reaction of the polymerizable maleimide group, forming a crosslinked polymeric layer and enabling the polymeric layer to cause photo-alignment.

5. The method of manufacturing a photo-alignment layer according to claim 4, wherein the maleimide compound is a compound represented by the general formula:

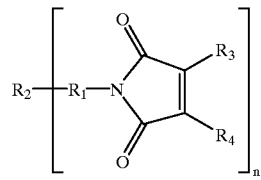

wherein:

$R_1$ represents:
an alkylene group having 1 to 30 carbon atoms, a cycloalkylene group having 3 to 12 carbon atoms, 2 to 5 molecular groups selected from the group of alkylene groups having 1 to 30 carbon atoms and cycloalkylene groups having 3 to 12 carbon atoms, the 2 to 5 molecular groups joined via a single bond, ester bond, ether bond or urethane bond; $R_2$ represents a photo-alignment moiety selected from the group consisting of a benzophenone group, cinnamoyl group, chalcone group, and coumarin group;

$R_3$ and $R_4$ each independently represents a hydrogen atom, an alkyl group having 1 to 8 carbon atoms, a phenyl group, or a halogen atom; and n represents an integer of 2 to 4.

6. A method of manufacturing a photo-alignment layer, which comprises:

coating a polymerizable monomer having at least one photo-alignment moiety, which causes a photo-alignment by a photo dimerization reaction, and at least two polymerizable maleimide groups in a polymerizable monomer on a substrate, heating the coating layer to cause a thermal polymerization reaction, thereby forming a crosslinked polymeric layer, and exposing the polymeric layer to light to cause a photo dimerization reaction of the photo-alignment moiety causing photo-alignment by photo dimerization, the polymeric layer causing photo-alignment.

7. The method of manufacturing a photo-alignment layer according to claim 6, wherein the maleimide compound is a compound represented by the general formula:

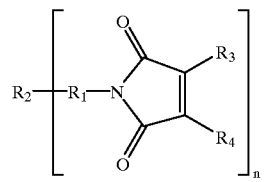

wherein:

$R_1$ represents:
an alkylene group having 1 to 30 carbon atoms, a cycloalkylene group having 3 to 12 carbon atoms, or 2 to 5 molecular groups selected from the group of alkylene groups having 1 to 30 carbon atoms and cycloalkylene groups having 3 to 12 carbon atoms, the 2 to 5 molecular groups joined via a single bond, ester bond, ether bond or urethane bond; $R_2$ represents a photo-alignment moiety selected from the group consisting of a benzophenone group, cinnamoyl group, chalcone groups and coumarin group;

R3 and R4 each independently represents a hydrogen atom, an alkyl group having 1 to 8 carbon atoms, a phenyl group, or a halogen atom; and n represents an integer of 2 to 4.

8. A liquid crystal display device having a structure comprising two substrates each having an alignment layer on its interior surface and liquid crystals interposed between the two substrates, wherein the alignment layer is a photo-alignment layer which comprises a polymer made of a polymerizable monomer having at least one photo-alignment moiety, which carries out a photo-alignment by a photo dimerization reaction, and at least two polymerizable maleimide groups per molecule, and also has the photo-alignment function caused by photo dimerization of the photo-alignment moiety and a crosslinked structure formed by polymerization of the polymerizable maleimide group.

9. The liquid crystal display device according to claim 8, wherein the maleimide compound is a compound represented by the general formula:

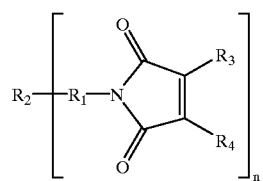

wherein:

$R_1$ represents:

an alkylene group having 1 to 30 carbon atoms, a cycloalkylene group having 3 to 12 carbon atoms, or 2 to 5 molecular groups selected from the group of alkylene groups having 1 to 30 carbon atoms and cycloalkylene groups having 3 to 12 carbon atoms, the 2 to 5 molecular group joined via a single bond, an ester bond, an ether bonds or a urethane bond;

$R_2$ represents a photo-alignment moiety selected from the group consisting of benzophenone group, cinnamoyl group, chalcone group and coumarin group;

$R_3$ and $R_4$ each independently represents a hydrogen atom, an alkyl group having 1 to 8 carbon atoms, a phenyl group, or a halogen atom; and n represents an integer of 2 to 4.

* * * * *